United States Patent [19]

Bowley et al.

[11] Patent Number: 4,907,875
[45] Date of Patent: Mar. 13, 1990

[54] DIAMOND SEPARATION PROCESS

[75] Inventors: Heather J. Bowley, Ashford; Donald L. Gerrard, West Ewell, both of England

[73] Assignee: The British Petroleum Company p.l.c., London, United Kingdom

[21] Appl. No.: 252,416

[22] PCT Filed: Jan. 14, 1988

[86] PCT No.: PCT/GB88/00022

§ 371 Date: Sep. 12, 1988

§ 102(e) Date: Sep. 12, 1988

[87] PCT Pub. No.: WO88/05534

PCT Pub. Date: Jul. 28, 1988

[30] Foreign Application Priority Data

Jan. 16, 1987 [GB] United Kingdom ............... 8700917

[51] Int. Cl.$^4$ ................... G01J 3/44; G01N 21/65; G01N 21/87
[52] U.S. Cl. ....................... 356/30; 209/581; 356/301
[58] Field of Search ............... 356/30, 301; 209/580, 209/581, 582

[56] References Cited

U.S. PATENT DOCUMENTS

| | | |
|---|---|---|
| 1,799,604 | 4/1931 | Read . |
| 4,030,827 | 6/1977 | Delhaye et al. ............ 356/301 |
| 4,259,011 | 3/1981 | Crumm et al. ............. 356/30 |
| 4,280,625 | 7/1981 | Grobbelaar et al. ......... 209/582 |
| 4,291,975 | 9/1981 | Raccah ..................... 356/30 |
| 4,397,556 | 8/1983 | Müller ..................... 356/301 |
| 4,482,245 | 11/1984 | Makabe et al. ............. 356/30 |
| 4,508,449 | 4/1985 | Okazaki ................... 356/30 |
| 4,527,895 | 7/1985 | Rubin ...................... 356/30 |

FOREIGN PATENT DOCUMENTS

| | | |
|---|---|---|
| 41348 | 12/1981 | European Pat. Off. . |
| 0064842 | 11/1982 | European Pat. Off. . |
| 0071462 | 2/1983 | European Pat. Off. . |
| 2915801 | 10/1980 | Fed. Rep. of Germany . |
| 3600115 | 7/1987 | Fed. Rep. of Germany . |
| 643142 | 9/1928 | France . |
| 2496888 | 6/1982 | France . |
| 1416568 | 12/1975 | United Kingdom . |
| 2010474 | 6/1979 | United Kingdom . |
| 2036360 | 6/1982 | United Kingdom . |
| 2056058 | 10/1983 | United Kingdom . |
| 2140555 | 11/1984 | United Kingdom . |
| 86/07457 | 12/1986 | World Int. Prop. O. . |

OTHER PUBLICATIONS

S. A. Solin et al., "Raman Spectrum of Diamond", Physical Review B, vol. 1, No. 4, Feb. 15, 1970, pp. 1687-1698.
Rabek, J. F., "Experimental Methods in Photochemistry and Photophysics", MIR Publishing House, Moscow, pp. 447-449, translated by Wiley, 1982, pp. 431-433.

Primary Examiner—F. L. Evans
Attorney, Agent, or Firm—Joseph G. Curatolo; George W. Moxon, II; Larry W. Evans

[57] ABSTRACT

A method of assessing the color type of diamonds by irradiating the diamonds with laser radiation of different wavelengths and generating a numerical value characteristic of the color type of the diamond based on the measured intensities of the resultant scattered Raman radiation for two or more different incident radiation wavelengths. The color type of the diamond may be determined by comparing derived relative intensities of each diamond with those of reference diamonds having been determined by standard subjective assessment. The method may also be used to sort diamonds according to their color type.

13 Claims, 2 Drawing Sheets

DIAMOND SEPARATION PROCESS

The present invention relates to the assessment of diamond colour and more particularly relates to the assessment of diamond colour by means of laser Raman spectroscopic techniques.

The colour of valuable gems such as diamonds is generally determined in a subjective manner. Thus a person allegedly expert in the art will examine the diamond by eye and then express an opinion as to its colour. However, the procedure is slow, requires considerable skill and in view of its subjectivity could be open to error.

The Raman signal of diamond is much stronger than that of other materials because diamond only contains carbon to carbon bonding and its Raman signal occurs at a position well separated from those of other minerals. Thus the Raman signal is highly specific for diamond. Also, because diamond only contains one type of carbon to carbon bond, there is only a single Raman signal which can be readily distinguished from associated broad band fluorescence.

Laser Raman spectroscopy may be used for the separation of diamonds from a diamondiferous material and a method using this technique is disclosed in our UK patent no. GB 2140555B. Laser Raman spectroscopy may also be used for assessing the quality of a diamond in an objective manner and a method using this technique is disclosed in our PCT patent application no. WO 87/03963. The method comprises the steps of calibrating a laser Raman spectrometer with diamonds of known quality characteristics, placing a diamond of unknown quality characteristic in a fixed orientation, passing incident laser radiation of known frequency and intensity onto the diamond, and monitoring the intensity of the scattered Raman signal for one or more orientations of the diamond of unknown quality.

It is an object of the present invention to provide means for assessing the colour type of a diamond in a less subjective manner than the known method of judgement by a human observer and it has been found that laser Raman spectroscopy may be used as a basis for an improved method of assessing the colour type of diamonds.

Thus according to the present invention there is provided a method of assessing the colour type of diamonds comprising the steps of (a) passing incident laser radiation of pre-determined intensity at two or more different, pre-determined wavelengths onto a diamond, the laser radiation being capable of causing Raman radiation to be scattered from the diamond, (b) measuring the intensity of the scattered Raman radiation from the diamond for each of the incident laser radiation wavelengths, (c) generating a numerical value characteristic of the colour type of the diamond based on the measured intensities of scattered Raman radiation for the two or more different incident laser radiation wavelengths.

According to a further aspect of the invention there is provided an apparatus for assessing the colour type of diamonds comprising, (a) means for irradiating a diamond with laser radiation of pre-determined intensity at two or more different, pre-determined wavelengths, the laser radiation being capable of causing Raman radiation to be scattered from the diamond, (b) means for measuring the intensity of the scattered Raman radiation from the diamond for each of the incident laser radiation wavelengths, (c) means for generating a numerical value characteristic of the colour type of the diamond based on the intensities of scattered Raman radiation for the two or more different incident laser radiation wavelengths.

It is preferred that the diamonds are of similar size range and thus it may be necessary to sort diamonds into size ranges prior to using the method and apparatus according to the present invention. The present invention may be used for the assessment of both cut and uncut diamonds.

The diamond may be irradiated with laser radiation of two or more wavelengths, either simultaneously or sequentially.

The source of laser radiation may be a single laser adapted to operate at two or more discrete, pre-determined wavelengths, simultaneously or sequentially. Alternatively two or more lasers may be used, each adapted to operate at one or more discrete, pre-determined wavelengths, simultaneously or sequentially. The diamond may be held or supported in the laser radiation by a holder. The diamond may be irradiated with laser radiation as it falls from the end of a conveyor belt or the like. Preferably the orientation of the diamonds with respect to the incident laser radiation is the same for each laser when more than one laser is used.

The scattered Raman radiation from the diamond being assessed is filtered from other types of radiation by a suitable optical arrangement such as a collection optic and monochromator. A detector such as a photomultiplier or multichannel detector (e.g. diode array detector) may be used to measure the intensity of the scattered Raman radiation. More than one detector, or a multichannel detector may be used to measure the intensities of scattered radiation at two or more different incident radiation wavelengths simultaneously.

The numerical value characteristic of the colour type of the diamond may be generated electronically by a computer or a microcomputer. Preferably, the numerical value is a relative intensity generated from the ratio of intensities of the scattered Raman radiation for two different incident laser radiation wavelengths.

It is envisaged that the method according to the present invention may be used to determine the colour type of diamonds by passing incident laser radiation of pre-determined intensity at two or more different, pre-determined wavelengths onto a diamond, the laser radiation being capable of causing Raman radiation to be scattered from the diamond, measuring the intensity of the scattered Raman radiation from the diamond for each of the incident laser radiation wavelengths, generating a numerical value characteristic of the colour type of the diamond based on the measured intensities of scattered Raman radiation for the two or more different incident laser radiation wavelengths, and comparing the generated numerical value with numerical values of diamonds of known colour type thereby to determine the colour type of the diamond. Preferably, the numerical value is a relative intensity generated from the ratio of intensities of scattered Raman radiation for two different incident laser radiation wavelengths. The numerical values may be compared by a computer or a microprocessor.

It is further envisaged that the method according to the present invention may be used to sort diamonds according to their colour type by passing incident laser radiation of pre-determined intensity at two or more different, pre-determined wavelengths onto a diamond, the laser radiation being capable of causing Raman radiation to be scattered from the diamond, measuring the intensity of the scattered Raman radiation from the diamond for each of the incident laser radiation wavelengths, generating a numerical value characteristic of the colour type of the diamond based on the measured intensities of scattered Raman radiation for the two or more different incident laser radiation wavelengths, and sorting the diamond according to the generated numerical value. Preferably, the numerical value is a relative intensity generated from the ratio of intensities of scattered Raman radiation for two different incident laser radiation wavelengths. Sorting of the diamond may be performed by conventional techniques such as compressed gas ejectors and the like. Preferably the sorting means is under the control of a computer or microprocessor which sorts the diamonds according to the generated numerical value.

The present invention may be adapted to a batch or continuous method of sorting diamonds into groups of known colour and quality from diamondiferous material. Thus, for example, the method of our UK patent no. GB 2140555B may be used to separate diamonds from diamondiferous material, the resultant diamonds then being sorted into portions of diamonds of known colour type by the method as hereinbefore described, the quality of the diamonds of each portion then being determined by the method of our PCT patent application No. WO 87/03963. The diamonds may be sorted according to colour type and quality simultaneously.

It is envisaged that the method of the present invention may be used for both natural and synthetic diamonds. Since it is believed that for synthetic diamonds the colour type is characteristic of the hardness of the diamond, the method and apparatus of the present invention may also be used for assessing the hardness of synthetic diamonds.

The invention will now be described by way of example only and with reference to the accompanying drawings.

Figure 1:
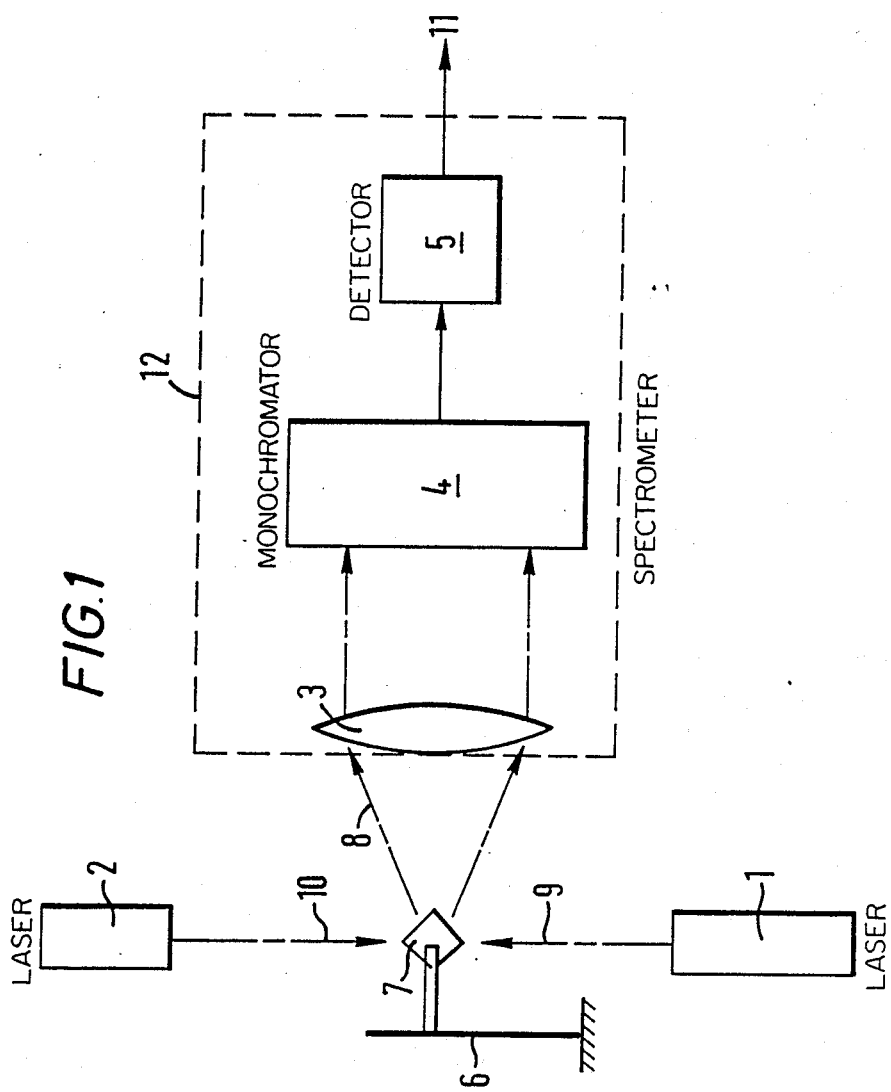
FIG. 1 is a schematic diagram of an apparatus for assessing diamond colour type according to the method of the present invention.

In FIG. 1, the apparatus has two sources (1), (2) of laser radiation (9) and (10) capable of causing Raman radiation (8) to be scattered from a diamond (7). Each source operates in a single wavelength mode i.e. only emitting a radiation of a single wavelength at one time. In this example the wavelength of laser radiation (9) from source (1) could be changed so that Raman intensities could be measured at two different wavelengths of incident radiation. The laser used for source (1) was a Spectra-Physics model 2020 argon ion laser capable of output at 488.0 nanometers (nm) and 514.5 nanometers (nm). The laser used for source (2) was operated in a single wavelength mode i.e. only emitting laser radiation (10) of a single wavelength. In this example, the laser used for source (2) was a Spectra-Physics model 164 Krypton ion laser capable of output at 647.1 nanometers (nm). Both lasers were operated in their "light" mode at 50 mw, thus maintaining constant photon flux.

A diamond holder (6) was capable of holding a diamond (7) in the laser radiation (9), (10) and was capable of varying the orientation of the diamond with respect to the direction of the laser radiation (9), (10).

In use, measurement of the scattered Raman radiation (8) was carried out using an Anaspec 36 laser-Raman spectrometer (12) comprising a collection optic (3), a monochromator, (4) and a Reticon type S intensified diode array detector (5). Alternative detectors may be used, for example, a photomultiplier. The detector gave a digital output (11) which was a measure of the intensity of the scattered Raman radiation (8).

In use, a diamond (7) was held in the holder (6) and laser radiation (9), (10) of different wavelengths from the lasers (1) and (2) was passed sequentially onto the diamond (7). The position of the diamond (7) in the holder (6) was optimised to obtain the maximum intensity of scattered Raman radiation (8) at the detector (5). The maximum intensity of the scattered Raman radiation was measured for several orientations of the diamond at each incident laser radiation wavelength. The total accumulation time (the time taken to count the number of photons in the scattered Raman radiation) was of the order of one second. The accumulation time required is dependent on the frequency of the incident laser radiation and the diamond colour type. The maximum intensities of the scattered Raman radiation are expressed in number of photons counted per second. As the spread of these intensities for different orientations of the diamond was small, a mean value of the intensities of the Raman signal for the diamond was calculated herein referred to as the mean Raman intensity. The mean Raman intensity was determined at each of three incident laser radiation wavelengths (514.5 nm, 488.0 nm and 647.1 nm) sequentially.

The results of an assessment of diamonds of colour types yellow and green are given in Tables 1 and 2. Table 1 gives results for type yellow diamonds of classes 1 to 7 and Table 2 gives results for type green diamonds of classes 1 to 6, class 1 being of the highest quality and class 7 being of the lowest quality. The colours and the qualities were originally determined by standard subjective assessment.

The mean Raman intensities at each of the three wavelengths of incident radiation are given for five samples of diamonds (where possible) for each quality class and colour type. The mean Raman intensities in each case are those calculated from five different orientations of the diamond in the holder. It was found that in each case the orientation of the diamond made little difference to the intensity of the Raman signal due to its tetrahedral carbon to carbon stretching mode.

Relative intensities are also given in the tables, where the relative intensities are defined as the ratio of the mean Raman intensities, that is $I_{514.5}/I_{488}$ and $I_{514.5}/I_{647.1}$, and where $I_{514.5}$ is the mean Raman intensity for an incident laser radiation of wavelength 514.5 nanometers, etc.

The tables show that the relative intensities are more or less constant and characteristic of the colour type i.e yellow diamonds have relative intensities of about 7 and 8 and green diamonds have relative intensities of about 4.

It is envisaged that in this example, the colour type of diamonds of unknown colour type may be determined by comparing derived relative intensities of the unknown diamonds with the derived relative intensities of these diamonds of known colour type.

Figure 2:
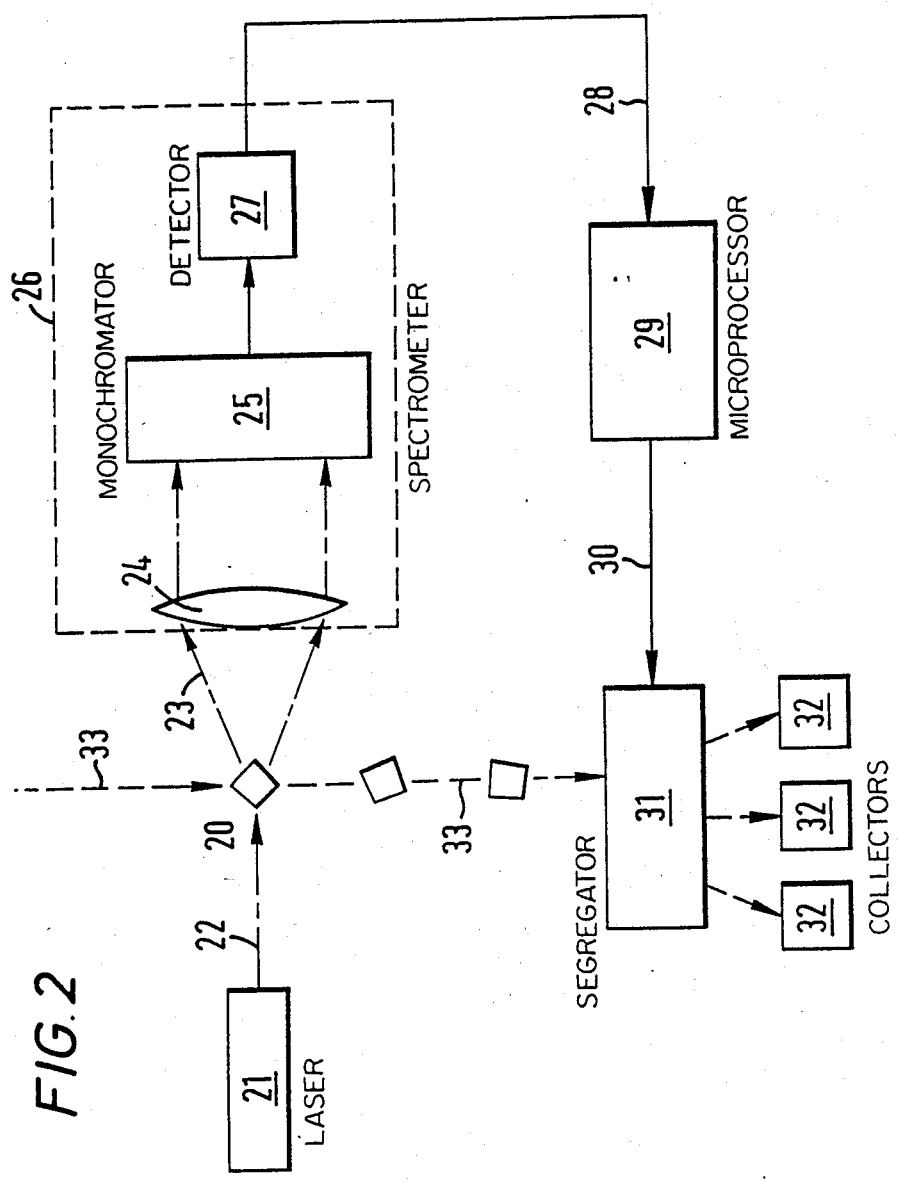
FIG. 2 is a schematic diagram of an apparatus for sorting diamonds according to their colour type according to the method of the present invention.

FIG. 2, is a schematic diagram of an apparatus for sorting diamonds according to their colour type according to the method of the present invention. Diamonds (20) are transported on a moving conveyor (33) through a beam of laser radiation (22) from a laser (21). The laser (21) is capable of operating at two or more discrete, pre-determined wavelengths simultaneously (all lines mode). Raman radiation (23) scattered from each diamond (20) is measured using a spectrometer (26) comprising a collection optic (24), a monochromator (25) and a multichannel detector (27). The detector (27) gives digital outputs (28) which are measures of the intensities of the scattered Raman radiation (23) for the two or more incident laser radiation wavelengths. A microprocessor (29) generates a numerical value characteristic of the diamond colour type from the measured intensities and transmits a suitable signal along line (30) to operate a segregator (31) according to the generated numerical value. Preferably, the numerical value is a relative intensity generated from the ratio of intensities of scattered Raman radiation for two different incident laser radiation wavelengths. The segregator (31) sorts the diamonds into collectors (32) according to the generated numerical value and hence colour type. The segregator (31) may be a group of conventional gas ejectors or the like.

TABLE 1

| Quality Class | Sample Number | Diamond Type - Yellow | | | | |
|---|---|---|---|---|---|---|
| | | Mean Raman Intensity (counts/sec) at Different Incident Radiation Wavelengths | | | Relative Intensities | |
| | | $\lambda e488.0$ | $\lambda e514.5$ | $\lambda e647.5$ | $I_{514.5}/I_{488}$ | $I_{514.5}/I_{647.1}$ |
| 1 | 1 | 24736 | 200 613 | 28295 | 8.11 | 7.09 |
| | 2 | 25136 | 200 588 | 28055 | 7.98 | 7.15 |
| | 3 | 25093 | 200 492 | 28198 | 7.99 | 7.11 |
| | 4 | — | — | — | — | — |
| | 5 | — | — | — | — | — |
| 2 | 1 | 20187 | 160 490 | 22732 | 7.95 | 7.06 |
| | 2 | 19988 | 160 101 | 22549 | 8.01 | 7.10 |
| | 3 | 19947 | 159 376 | 22384 | 7.99 | 7.12 |
| | 4 | 19551 | 158 954 | 22675 | 8.13 | 7.01 |
| | 5 | 19729 | 158 627 | 22726 | 8.04 | 6.98 |
| 3 | 1 | 16704 | 133 461 | 18981 | 7.99 | 7.03 |
| | 2 | 16374 | 133 450 | 18789 | 8.15 | 7.10 |
| | 3 | 16497 | 132 968 | 19019 | 8.06 | 6.99 |
| | 4 | 16419 | 132 919 | 18898 | 8.10 | 7.03 |
| | 5 | 16621 | 132 888 | 18716 | 7.99 | 7.10 |
| 4 | 1 | 14536 | 116 204 | 16374 | 7.99 | 7.01 |
| | 2 | 14708 | 116 201 | 16502 | 7.90 | 7.04 |
| | 3 | 14314 | 115 972 | 16257 | 8.10 | 7.13 |
| | 4 | 14376 | 115 927 | 16575 | 8.06 | 6.99 |
| | 5 | 14608 | 115 883 | 16325 | 7.93 | 7.10 |
| 5 | 1 | 12927 | 103 467 | 14549 | 8.00 | 7.11 |
| | 2 | 12722 | 102 978 | 14649 | 8.09 | 7.03 |
| | 3 | — | — | — | — | — |
| | 4 | — | — | — | — | — |
| | 5 | — | — | — | — | — |
| 6 | 1 | 10186 | 81005 | 11523 | 7.05 | 7.03 |
| | 2 | 10246 | 80834 | 11386 | 7.89 | 7.01 |
| | 3 | 10062 | 80609 | 11525 | 8.01 | 6.99 |
| | 4 | 10067 | 80133 | 11360 | 7.96 | 7.05 |
| | 5 | — | — | — | — | — |
| 7 | 1 | 9512 | 74958 | 10733 | 7.88 | 6.98 |
| | 2 | — | — | — | — | — |
| | 3 | — | — | — | — | — |
| | 4 | — | — | — | — | — |
| | 5 | — | — | — | — | — |

TABLE 2

| Quality Class | Sample Number | Diamond Type - Green | | | | |
|---|---|---|---|---|---|---|
| | | Mean Raman Intensity (counts/sec) at Different Incident Radiation Wavelengths | | | Relative Intensities | |
| | | $\lambda e488.0$ | $\lambda e514.5$ | $\lambda e647.1$ | $I_{514.5}/I_{488}$ | $I_{514.5}/I_{647.1}$ |
| 1 | 1 | 16790 | 67355 | 16988 | 4.01 | 3.96 |
| | 2 | 16363 | 67326 | 16737 | 4.11 | 4.02 |
| | 3 | 16424 | 66839 | 16352 | 4.07 | 4.09 |
| | 4 | 16443 | 65814 | 16506 | 4.00 | 3.98 |
| | 5 | 15840 | 65787 | 15989 | 4.15 | 4.11 |
| 2 | 1 | 12247 | 49755 | 12093 | 4.06 | 4.11 |
| | 2 | 12114 | 49658 | 12279 | 4.01 | 4.04 |
| | 3 | 12006 | 49616 | 12059 | 4.13 | 4.11 |
| | 4 | 12139 | 49383 | 12241 | 4.07 | 4.03 |
| | 5 | 12103 | 49072 | 11987 | 4.05 | 4.09 |
| 3 | 1 | 11242 | 45301 | 11146 | 4.03 | 4.06 |
| | 2 | 11058 | 45273 | 11206 | 4.09 | 4.04 |
| | 3 | 10928 | 44796 | 11032 | 4.01 | 4.06 |
| | 4 | 10858 | 44135 | 10669 | 4.06 | 4.13 |
| | 5 | 10641 | 43517 | 10789 | 4.09 | 4.03 |
| 4 | 1 | 10293 | 41759 | 10351 | 4.06 | 4.03 |
| | 2 | 9955 | 40958 | 9877 | 4.11 | 4.15 |
| | 3 | 9876 | 40531 | 10063 | 4.10 | 4.03 |
| | 4 | 9653 | 39467 | 9821 | 4.09 | 4.02 |
| | 5 | 9824 | 39401 | 9712 | 4.01 | 4.06 |
| 5 | 1 | 8608 | 35289 | 8750 | 4.10 | 4.03 |
| | 2 | 8147 | 32705 | 8229 | 4.01 | 3.97 |
| | 3 | 7935 | 31642 | 7719 | 3.99 | 4.10 |
| | 4 | 7017 | 27677 | 7089 | 3.94 | 3.90 |
| | 5 | 6067 | 23552 | 6115 | 3.88 | 3.85 |
| 6 | 1 | 3546 | 14015 | 3599 | 3.95 | 3.89 |
| | 2 | 977 | 3584 | 993 | 3.67 | 3.61 |
| | 3 | — | — | — | — | — |
| | 4 | — | — | — | — | — |
| | 5 | — | — | — | — | — |

We claim:

1. A method of assessing the colour type of diamonds comprising the steps of (a) passing incident laser radiation of pre-determined intensity at two or more different, pre-determined wavelengths onto a diamond, the laser radiation being capable of causing Raman radiation to be scattered from the diamond, (b) measuring the intensity of the scattered Raman radiation from the diamond for each of the incident laser radiation wavelengths, (c) generating a numerical value characteristic of the colour type of the diamond based on the measured intensities of scattered Raman radiation for the two or more different incident laser radiation wavelengths.

2. A method of assessing the colour type of diamonds according to claim 1 in which the numerical value characteristic of the diamond colour type of the diamond is a relative intensity generated from the ratio of intensities of scattered Raman radiation for two different incident laser radiation wavelengths.

3. A method according to claim 1 in which the incident laser radiation has a wavelength of 488.0 nanometers, 514.5 nanometers or 647.5 nanometers.

4. A method according to claim 1 in which the diamonds are sorted into a known size range prior to assessment.

5. A method according to claim 1 in which the diamonds to be assessed are natural diamonds.

6. A method according to claim 1 in which the diamonds to be assessed are synthetic diamonds.

7. A method according to claim 1 in which the incident laser radiation is passed onto the diamond at more than one wavelength simultaneously.

8. A method according to claim 1 in which the incident laser radiation is passed onto the diamond at more than one wavelength sequentially.

9. An apparatus for assessing the colour type of diamonds comprising, (a) means for irradiating a diamond with laser radiation of pre-determined intensity at two or more different, pre-determined wavelengths, the laser radiation being capable of causing Raman radiation to be scattered from the diamond, (b) means for measuring the intensity of the scattered Raman radiation from the diamond for each of the incident laser radiation wavelengths, (c) means for generating a numerical valve characteristic of the colour type of the diamond based on the intensities of scattered Raman radiation for the two or more different laser radiation wavelengths.

10. A method of determining the colour type of diamonds comprising the steps of (a) passing incident laser radiation of pre-determined intensity at two or more different, pre-determined wavelengths onto a diamond, the laser radiation being capable of causing Raman radiation to be scattered from the diamond, (b) measuring the intensity of the scattered Raman radiation from the diamond for each of the incident laser radiation wavelengths, (c) generating a numerical value characteristic of the colour type of the diamond based on the measured intensities of scattered Raman radiation for the two or more different incident laser radiation wavelengths, (d) comparing the numerical value with numerical values of diamonds of known colour type thereby to determine the colour type of the diamond.

11. A method of determining the colour type of diamonds according to claim 10 in which the generated numerical value is a relative intensity generated from the ratio of intensities of scattered Raman radiation for two different incident laser radiation wavelengths.

12. A method of sorting diamonds according to their colour type comprising (a) passing incident laser radiation of pre-determined intensity at two or more different, pre-determined wavelengths onto a diamond, the laser radiation being capable of causing Raman radiation to be scattered from the diamond, (b) measuring the intensity of the scattered Raman radiation from the diamond for each of the incident laser radiation wavelengths, (c) generating a numerical value characteristic of the colour type of the diamond based on the measured intensities of scattered Raman radiation for the two or more different incident laser radiation wavelengths, (d) sorting the diamond according to the generated numerical value.

13. A method of sorting diamonds according to their colour type according to claim 12 in which the generated numerical value is a relative intensity generated from the ratio of intensities of scattered Raman radiation for two different incident laser radiation wavelengths.

* * * * *